(12) United States Patent
Fu et al.

(10) Patent No.: US 12,673,029 B2
(45) Date of Patent: Jul. 7, 2026

(54) NANODELIVERY SYSTEM BASED ON GLOBULIN-1 S ALLELE, PREPARATION METHOD THEREFOR AND USE THEREOF

(71) Applicant: Zhejiang Gongshang University, Hangzhou (CN)

(72) Inventors: Linglin Fu, Hangzhou (CN); Chong Wang, Hangzhou (CN); Jinru Zhou, Hangzhou (CN); Li Wang, Hangzhou (CN); Shunyu Wang, Hangzhou (CN)

(73) Assignee: Zhejiang Gongshang University, Hangzhou (CN)

( * ) Notice: Subject to any disclaimer, the term of this patent is extended or adjusted under 35 U.S.C. 154(b) by 288 days.

(21) Appl. No.: 18/241,928

(22) Filed: Sep. 4, 2023

(65) Prior Publication Data

US 2024/0099983 A1 Mar. 28, 2024

(30) Foreign Application Priority Data

Sep. 26, 2022 (CN) .......................... 202211179994.9

(51) Int. Cl.
A61K 9/51 (2006.01)
A61K 9/08 (2006.01)

(52) U.S. Cl.
CPC .............. A61K 9/5176 (2013.01); A61K 9/08 (2013.01)

(58) Field of Classification Search
CPC .................................................. A61K 9/5176
See application file for complete search history.

(56) References Cited

U.S. PATENT DOCUMENTS

2021/0230090 A1* 7/2021 Ramirez Rios .......... A61K 8/11

FOREIGN PATENT DOCUMENTS

CN 102657866 A * 9/2012

OTHER PUBLICATIONS

Colloidal solution. the globulins. J Physiol. Dec. 30, 1905;33(4-5):251â337. doi: 10.1113/jphysiol.1905.sp001126 (Year: 1905).*
(2018). Baking Quality Improvement in Wheat Flour by Physical Mutagenesis, p. 66 (Year: 2018).*

* cited by examiner

*Primary Examiner* — Benjamin J Packard

(57) ABSTRACT

A nanodelivery system based on globulin-1 S allele, a preparation method therefor and use thereof are provided. The preparation method includes the following steps of: dissolving globulin-1 S allele in a NaCl solution, and performing magnetical stirring until the globulin-1 S allele is completely dissolved to obtain a mixed solution; self-assembly: centrifuging the mixed solution, taking the supernatant to be dispersed into a dispersion solution for self-assembly to obtain a globulin-1 S allele dispersion; and adding hydrophobic plant polyphenol to the globulin-1 S allele dispersion, performing well mixing and centrifuging, and removing the supernatant to obtain the nanodelivery system based on the globulin-1 S allele.

6 Claims, 3 Drawing Sheets

**Result analysis of light stability of curcumin
and a GSA protein-curcumin complex**

NANODELIVERY SYSTEM BASED ON GLOBULIN-1 S ALLELE, PREPARATION METHOD THEREFOR AND USE THEREOF

CROSS REFERENCE TO THE RELATED APPLICATIONS

This application is based upon and claims priority to Chinese Patent Application No. 202211179994.9, filed on Sep. 26, 2022, the entire contents of which are incorporated herein by reference.

TECHNICAL FIELD

The present disclosure relates to the field of biotechnology, in particular to a nanodelivery system based on globulin-1 S allele, a preparation method therefor and use thereof.

BACKGROUND

The size of nanoparticles is approximately a few hundred nanometers, the smaller particle size determines their unique physicochemical properties, making them particularly prominent in a variety of biological applications, and nanomaterials exhibit high surface area-to-volume ratios, and their functions in vivo can be altered by functional modifications of their surfaces and grafting of ligands and the like. Nanocarriers can not only improve drug targeting and achieve controlled release, but also help to improve drug circulation time and solubility in vivo, intracellular delivery, and penetration of biological membranes. A nanodelivery system is a translucent or opaque suspension stable system formed spontaneously from protein, polysaccharide, an organic solvent, a surfactant and the like in an appropriate ratio, and can be used as a steady-state delivery system of nutritional factors such as vitamins, functional lipids, probiotics and polyphenolic compounds, and is widely used in the fields of food, medicine and the like. Studies have shown that a suitable nanodelivery system, for whether polar or non-polar nutrients, active factors and drugs, can improve their stability and duration of action, as well as the range of processing applications.

In recent years, the demand for biocompatible proteins based on nanoparticles in biotechnological fields such as food and medicine is increasing, and more research using these nanocarriers is expected. Proteins extracted from plants have been widely used as drug delivery carriers and substitutes for animal proteins due to the risk of contamination of infectious pathogens contained in animal tissues, as well as personal preferences. Food-based proteins are not only biodegradable and biocompatible, but also relatively inexpensive, renewable and easy to process, with reduced accumulation of particulate by-products, and minimized host immune response, making them more attractive in drug delivery and more valuable for human health. In addition to safety, clinical application should be considered. Clearly, in vivo and biological analysis is essential for drawing correct conclusions about safety, dosage, pharmacological activity, and the fate of these nanosystems. However, these results suggest that food protein-based nanocarriers are suitable tools for hydrophobic and poorly soluble molecular drug delivery. Among food proteins, globulin-1 S allele (GSA) is glycosylated wheat sensitizing protein. Insoluble substances include phenolic compounds, vitamins and essential oils and the like which are essential to human health and products used in the food and pharmaceutical industries such as essences, spices and food colorants. Curcumin (Cur) is a bioactive polyphenolic compound extracted from *Curcuma longa* rhizomes, and is currently one of the natural food pigments with the highest sales volume in the world. In addition to having a variety of pharmacological activities (such as antioxidant, antibacterial, anti-inflammatory and anti-cancer activities), curcumin is also widely used worldwide as spices (such as curry), a flavoring agent, etc. However, curcumin has very low water solubility, poor stability, easy oxidation, and susceptibility to photodegradation, which greatly limits its clinical effects and practical application.

Currently, a nanodelivery system based on globulin-1 S allele for the delivery of insoluble compounds has not been reported.

SUMMARY

The present disclosure aims to solve one of the technical problems in the related art at least to some extent.

The present disclosure uses a novel food-grade green chemistry method, namely globulin-1 S allele binds to an insoluble substance (such as curcumin) to achieve the purpose of transporting insoluble or poorly soluble substances.

One object of the present disclosure is to provide a nanodelivery system packaging kit for transporting insoluble compounds, which provides a new tool and a new technical method for related research and applications in the fields of biology, medicine and the like.

The present disclosure provides a nanodelivery system based on globulin-1 S allele, including a carrier and hydrophobic plant polyphenol, wherein the carrier is globulin-1 S allele, and the hydrophobic plant polyphenol is curcumin or hesperetin.

Globulin-1 S allele (GSA) is also known as wheat GSA protein.

The wheat GSA protein has good biocompatibility, is easily prepared into microparticles or nanoparticles, and can be used as an ideal carrier for hydrophobic drugs or functionally active ingredients.

The present disclosure also provides a preparation method for the nanodelivery system based on the globulin-1 S allele, including the following steps of:

(1) dissolving globulin-1 S allele in a NaCl solution, and performing magnetical stirring until the globulin-1 S allele is completely dissolved to obtain a mixed solution;

(2) self-assembly: centrifuging the mixed solution in the step (1), and taking the supernatant to be dispersed into a dispersion solution for self-assembly to obtain a globulin-1 S allele dispersion; and (3) adding hydrophobic plant polyphenol to the globulin-1 S allele dispersion in (2), conducting well mixing and centrifuging, and removing the supernatant to obtain the nanodelivery system based on the globulin-1 S allele;

wherein the hydrophobic plant polyphenol is curcumin or hesperetin.

Preferably, a concentration ratio of the hydrophobic plant polyphenol added in the step (3) to the globulin-1 S allele ranges from 1-10:1.

Preferably, a dispersing method in the step (2) includes: dropwise dispersing the supernatant obtained after centrifuging into the dispersion solution. A volume ratio of the supernatant to the dispersion solution in the step (2) is 2-5:1. The dispersion solution in the step (2) has a pH value of 6.5-7.5.

Preferably, the NaCl solution in the step (1) has a mass fraction of 5%-15%.

More preferably, the NaCl solution in the step (1) has a mass fraction of 10%.

The present disclosure also provides use of the nanodelivery system based on the globulin-1 S allele in functional foods or drugs.

The beneficial effects of the present disclosure are as follows:

the nanodelivery system based on the globulin-1 S allele of the present disclosure uses the wheat GSA protein as a delivery system, for example, curcumin is embedded to be prepared into particles in order to increase the stability of curcumin, extend its release time, improve the application value of curcumin and its products in foods and drugs, while providing a theoretical and application reference for the high-value utilization of the wheat GSA protein.

DETAILED DESCRIPTION OF THE EMBODIMENTS

Example 1

Figures 1, 2:
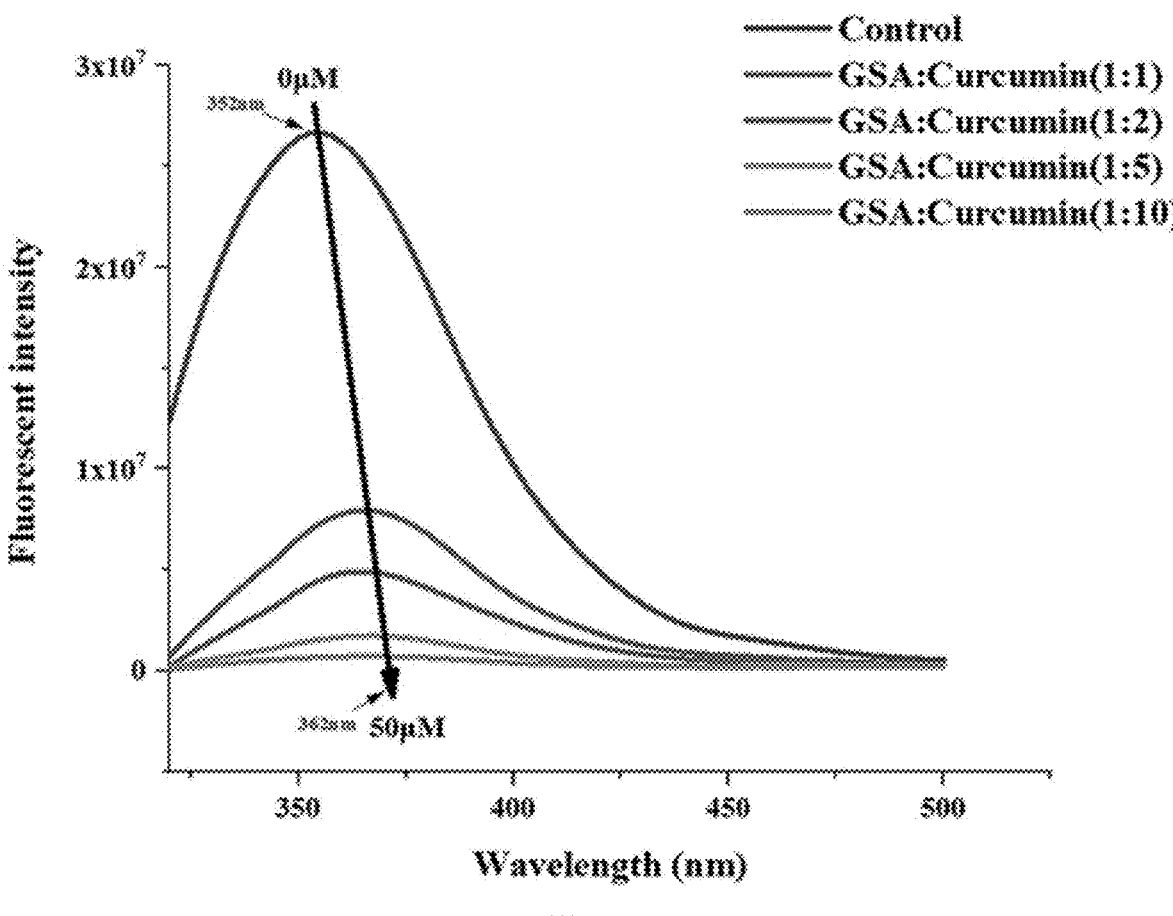
FIG. 1 is a fluorescence emission spectrum of GSA at a certain temperature and concentration under different curcumin concentrations.
FIG. 2 is a Stern-Volmer diagram of quenching wheat GSA protein by curcumin at different concentrations and temperatures.

Extraction and purification of wheat GSA protein.

GSA protein was extracted from Chinese spring wheat. Flour was defatted with acetone, was dissolved in phosphate buffered saline (PBS), and was filtered with a 0.45 μm filter membrane, and separation was performed by an ÄKTA pure25 protein purifier using a Hitrap ConA 4B chromatographic column, an elution peak was collected, and concentrated by ultrafiltration, and the solution was replaced with PBS, resulting in purified wheat GSA protein.

An equilibration buffer used for separation: 20 mmol/L of Tris-HCl, 0.3 mol/L of NaCl, 2 mmol/L of MnCl$_2$ and 2 mmol/L of CaCl$_2$), with a pH of 7.4; and an elution buffer: 20 mmol/L of Tris-HCl, 0.3 mol/L of NaCl, and 0.3 mol/L of methyl α-D-glucopyranoside, with a pH of 7.4.

Example 2

Self-assembly of wheat GSA protein nanoparticles.

Wheat GSA protein was dissolved in 10 mL of a NaCl solution with a mass fraction of 10% as a solvent to obtain GSA protein with a final concentration of 1 μM, magnetical stirring was performed until the wheat GSA protein was completely dissolved; and centrifuging was performed at 3,000 r/min for 10 min. 0.7 mL of The supernatant was taken to be dropwise dispersed into 2 mL of a dispersion solution (ultrapure water) under vortex oscillation conditions, so that the wheat GSA protein was self-assembled into nanoprotein particles.

Self-assembly of wheat GSA protein-curcumin composite nanoparticles.

To optimize the conditions for wheat GSA protein-curcumin self-assembled composite nanoparticles, wheat GSA protein-curcumin composite nanoparticles were prepared by using different NaCl concentrations (a mass fraction was 5%, 7.5%, 10%, 12.5%, and 15%, respectively) and different pH values of a dispersion solution (6.5, 7.0, and 7.5).

Preferably, GSA protein was dissolved with a NaCl solution with a mass fraction of 10% to obtain wheat GSA protein with a final concentration of 1 μM, magnetical stirring was performed until the GSA protein was completely dissolved, and wheat GSA protein nanoparticles coated with curcumin were prepared at a pH of the dispersion solution being 7.0. To the wheat GSA protein solution, curcumin was added at a certain concentration ratio (1:1, 1:2, 1:5, 1:10), and stirring was continuously performed at a constant temperature of 50° C. for 2-3 h to sufficiently fuse the wheat GSA protein and curcumin to obtain a curcumin-wheat GSA protein mixed solution, separation was performed by centrifugation, the supernatant was removed, and freeze-drying was performed to obtain powdered curcumin-wheat GSA protein composite nanoparticles. The preparation process should be kept in a dark place to avoid the decomposition of curcumin in the presence of light.

Example 3

Determination of of the binding force of wheat GSA protein to curcumin.

A wheat GSA protein solution and a curcumin solution were mixed in a certain ratio (1:1, 1:2, 1:5, 1:10) at different temperatures (298 K, 303 K, 310 K) for 2 hours. The final concentration of GSA was 1 μM, wherein the molecular weight of GSA was 56.16 KDa and the concentration of curcumin was 1 μM, 2 μM, 5 μM and 10 μM. The excitation spectrum was set at 280 nm, the emission spectrum was from 320 nm to 500 nm, and the recording temperature was 298 K, 303 K, and 310 K.

By exciting tyrosine (Tyr), phenylalanine (Phe) and tryptophan (Trp) residues, it was found that the protein has intrinsic fluorescence, which can be used for a binding interaction index. At an excitation wavelength of 280 nm, tryptophan and tyrosine residues will be excited. Binding of proteins and small molecules will lead to a decrease in fluorescence emission. Fluorescence spectra of wheat GSA protein bound to different concentrations of curcumin are shown in FIG. 1. As the concentration of curcumin increased, the fluorescence intensity decreased constantly and a slight red shift appeared. This suggests that the binding of GSA to curcumin changed the polarity of microenvironment around tryptophan and tyrosine residues.

Fluorescence quenching can be divided into dynamic quenching and static quenching. A dynamic quenching process can be distinguished by a Stern-Volmer equation:

$$F_0/F = 1 + K_{SV}[Q] = 1 + K_q \tau_0[Q] \tag{1}$$

wherein $F_0$ and F are the GSA fluorescence intensity of the system in the absence and presence of curcumin, respectively; [Q] is the concentration of a quencher curcumin; and $K_q$ is a fluorescence quenching rate constant. $K_{SV}$ is a Stern-Volmer dynamic quenching constant, determined by linear regression of a curve of $F_0/F$ versus [Q]; $\tau_0$ is an average service life of a fluorescent substance in the absence of a quencher; the curve of $F_0/F$ versus [Q] at different temperatures was plotted according to the Stern-Volmer equation, as shown in FIG. 2, and the results showed that a slope of the curve increased with the increase of the temperature, indicating that a quenching mechanism is dynamic quenching.

The values of $K_{SV}$, $K_q$ and a regression coefficient $R^2$ being all greater than 0.99 at the three temperatures (298 K, 303 K, and 309 K) are shown in Table 1, indicating that this linear equation is suitable for quenching modeling.

TABLE 1

| Quenching constant of interaction between GSA and curcumin at different temperatures | | | |
| --- | --- | --- | --- |
| T (K) | $K_{SV}$ ($10^5$ L/mol) | $K_q$ ($10^{13}$ L/mol*s) | $R^2$ |
| 298 | 1.3981 | 1.3981 | 0.9962 |
| 303 | 2.0211 | 2.0211 | 0.9901 |
| 310 | 3.0636 | 3.0636 | 0.9996 |

Figure 3:
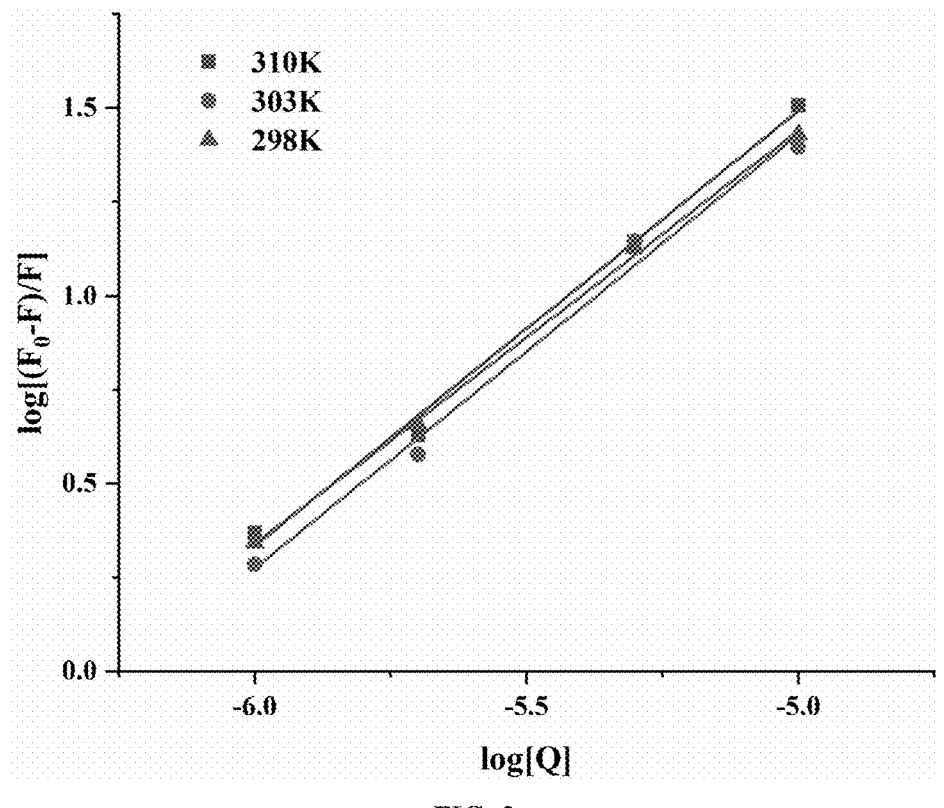
FIG. 3 is a Lineweaver-Burk diagram of fluorescence quenching between wheat GSA protein and curcumin.

Values for a static quenching mechanism, a binding constant and the number of binding sites can be obtained from a Lineweaver-Burk equation:

$$\log[(F_0-F)/F]=\log(Ka)+n\ \log[Q] \qquad (2)$$

wherein Ka is a binding constant, [Q] is the concentration of curcumin, and n is the number of binding sites. A log-log plot of $\log[(F_0-F)/F]$ versus $\log[Q]$ was made at 298 K, 303 K, and 310 K, respectively, according to the equation, as shown in FIG. 3. Ka and n at different temperatures were obtained from the intercept and slope. As shown in Table 2, n of binding curcumin to GSA at 298 K, 303 K, and 310 K is close to 1, and the Ka value is on the order of $10^6$, indicating that curcumin has one binding site with GSA. Curcumin has strong binding to GSA, which also indicates that GSA has a strong interaction with curcumin.

TABLE 2

| Binding constant of interaction between GSA and curcumin at different temperatures and corresponding thermodynamic parameters | | | | | | |
| --- | --- | --- | --- | --- | --- | --- |
| T (K) | Ka ($10^6$ L/mol) | n | $R^2$ | $\Delta H$ (kJ/mol) | $\Delta S$ (J/mol) | $\Delta G$ (kJ/mol) |
| 298 | 8.5822 | 1.099 | 0.9963 | 91.441 | 439.583 | −39.553 |
| 303 | 15.7797 | 1.1540 | 0.9909 | | | −41.751 |
| 310 | 16.9238 | 1.1593 | 0.9992 | | | −44.828 |

To determine the action force between GSA and curcumin, the temperature-dependent thermodynamic parameters ($\Delta G$, $\Delta H$, and $\Delta S$) were calculated using the following equations:

$$-lnK==-\Delta H/RT+\Delta S/R\ \Delta G=\Delta H-T\Delta S \qquad (3)$$

wherein R is a gas constant (8.314 J/mol*K), and T is the experimental temperature. As shown in Table 2, the positive values of $\Delta S$ and $\Delta H$ indicate that the main driving force of binding GSA to curcumin is hydrophobic interaction. Furthermore, $\Delta G<0$ indicates that binding of GSA to curcumin is a spontaneous process.

Example 4

Light stability assay of wheat GSA protein-curcumin composite nanoparticles.

0.93 mg of curcumin and 14.96 mg of wheat GSA protein-curcumin composite nanoparticles were accurately weighed to be separately put in petri dishes, and were irradiated at a close range with a 30 W UV lamp, sampling was performed at 0 h, 1 h, 2 h, 3 h, 4 h, 5 h, and 6 h, the samples were separately dissolved with a 10% sodium chloride solution, a volume was made up to a constant volume of 250 mL, 10 mL of the prepared solution was taken, and an absorbance at 426 nm was measured, wherein the absorbance was measured for three times to take an average.

Figure 4:
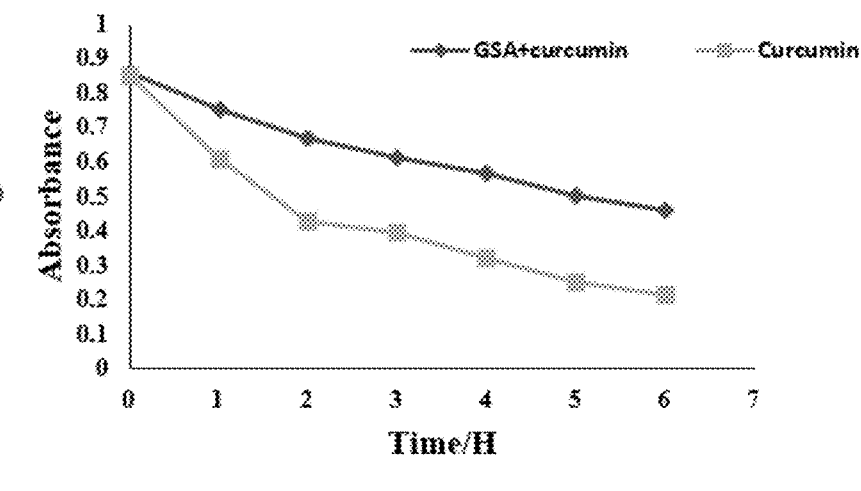
FIG. 4 is a result analysis diagram of light stability of curcumin and a wheat GSA protein-curcumin complex.

As shown in FIG. 4, UV irradiation resulted in a slower rate of decrease in absorbance of the composite nanoparticle sample than that of the curcumin sample. 2 h of UV irradiation resulted in a rapid decrease in absorbance of curcumin to 0.606, followed by a slower rate of decrease, and the absorbance was 0.252 and 0.214, respectively after 5 h and 6 h of of UV irradiation.

After 6 h of UV irradiation, the absorbance of curcumin decreased by 75%, while the absorbance of the composite particles decreased by 54%, thereby demonstrating that the composite particles have better light stability compared with curcumin. 6 h of UV irradiation increased the light stability of curcumin by 21% and extended the release time, because after curcumin interacts with wheat GSA protein, wheat globulin structurally protects the curcumin molecule, reducing its sensitivity to light, thereby increasing the light stability of curcumin after binding to some extent.

Example 5

Biological activity assay of curcumin in cellular experiments.

Curcumin has been proved to have powerful anti-inflammatory, anti-mutational and anti-cancer properties. In recent years, curcumin has been gradually recognized as a multipotent immunomodulator that can regulate the activation of immune cells. Some studies have explored the effects of curcumin on immune cells in animals and its mechanism, and found that treatment of immune cells with curcumin can significantly reduce cytokines produced by dendritic cells. On the basis of this study, the following experiment was performed by using the effects of dendritic cells and curcumin.

Dendritic cells DC2.4 were sensitized by treatment with ovalbumin (OVA) and cultured for 24 hours with curcumin and wheat GSA protein-curcumin composite nanoparticles as experimental groups, respectively, and relevant experiments were conducted. Total RNA was extracted from the cells, and subjected to reverse transcription according to the instructions to obtain cDNA of relevant cells, and a quantitative reverse transcription polymerase chain reaction (qRT-PCR) was carried out by using a real-time fluorescence quantitative PCR system.

Figure 5:
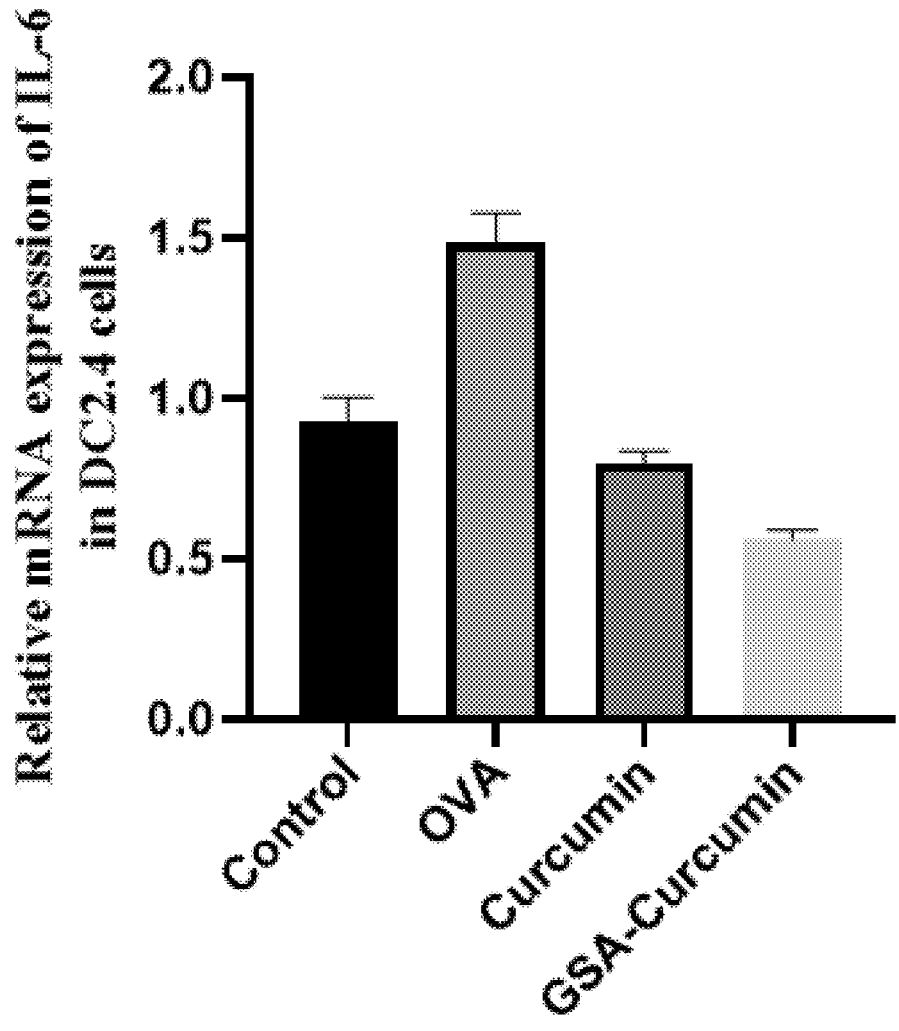
FIG. 5 is a result analysis diagram of the relative mRNA expression of DC-related genes regulated by a wheat GSA protein-curcumin complex.

As shown in FIG. 5, compared with untreated cells, DC2.4 cells stimulated by OVA for 24 hours produced a higher level of relevant pro-inflammatory cytokines (such as IL-6), curcumin has a certain alleviating effect on the allergic effect produced by OVA, compared with curcumin stimulation alone, the alleviating effect of the wheat GSA protein-curcumin composite nanoparticles on the allergic effect produced by OVA was better, and the above results showed that after exposure to curcumin, the ability of dendritic cells to produce a large amount of pro-inflammatory cytokines is impaired, and the wheat GSA protein-curcumin composite nanoparticles increases the bioaccessibility of curcumin during the alleviating effect, and increase the effect and time of action of curcumin in the cells.

What is claimed is:

1. A preparation method for a nanodelivery system based on a globulin-1 S allele, wherein the nanodelivery system based on the globulin-1 S allele comprises a carrier and a hydrophobic plant polyphenol, and the carrier is the globulin-1 S allele, and the hydrophobic plant polyphenol is curcumin or hesperetin; and the nanodelivery system based on the globulin-1 S allele is nanoparticles;

the method comprises the following steps of:

(1) dissolving the globulin-1 S allele in a NaCl solution to obtain a globulin-1 S allele-containing NaCl solution, and performing a magnetical stirring on the globulin-1 S allele-containing NaCl solution until the globulin-1 S allele is completely dissolved to obtain a mixed solution;

(2) a self-assembly: centrifuging the mixed solution in the step (1) to obtain a first supernatant, and taking the first supernatant into a dispersion solution for the self-assembly to obtain a globulin-1 S allele dispersion; and (3) adding the hydrophobic plant polyphenol to the globulin-1 S allele dispersion in the step (2) to obtain a hydrophobic plant polyphenol-containing globulin-1 S allele dispersion, conducting well mixing and centrifuging on the hydrophobic plant polyphenol-containing globulin-1 S allele dispersion to obtain a second supernatant, and removing the second supernatant to obtain the nanodelivery system based on the globulin-1 S allele.

2. The preparation method according to claim 1, wherein a concentration ratio of the hydrophobic plant polyphenol added in the step (3) to the globulin-1 S allele dispersion ranges from (1-10):1.

3. The preparation method according to claim 1, wherein a dispersing method in the step (2) comprises: dropwise dispersing the first supernatant obtained after the centrifuging into the dispersion solution.

4. The preparation method according to claim 1, wherein a volume ratio of the first supernatant to the dispersion solution in the step (2) is (2-5):1.

5. The preparation method according to claim 1, wherein the dispersion solution in the step (2) has a pH value of 6.5-7.5.

6. The preparation method according to claim 1, wherein the NaCl solution in the step (1) has a mass fraction of 5%-15%.

* * * * *